United States Patent [19]

Martinsson et al.

[11] 3,932,495

[45] Jan. 13, 1976

[54] PROCESS FOR PREPARING QUATERNARY AMMONIUM COMPOUNDS

[75] Inventors: Eva Margareta Martinsson, Stenungsund; Karl Martin Edvin Hellsten, Odsmal, both of Sweden

[73] Assignee: Modokemi Aktiebolag, Stenungsund, Sweden

[22] Filed: Aug. 27, 1974

[21] Appl. No.: 501,115

Related U.S. Application Data

[63] Continuation-in-part of Ser. Nos. 306,251, Nov. 10, 1972, abandoned, and Ser. No. 423,592, Dec. 10, 1973.

[30] Foreign Application Priority Data

Nov. 19, 1971 Sweden .............................. 14793/71
Oct. 11, 1972 Sweden .............................. 13069/72

[52] U.S. Cl. .......................................... 260/567.6 M
[51] Int. Cl.[2] .......................................... C07C 85/06

[58] Field of Search .............................. 260/567.6 M

[56] References Cited

FOREIGN PATENTS OR APPLICATIONS 2,256,234 5/1973 Germany ..................... 260/567.6 M

*Primary Examiner*—James O. Thomas, Jr.
*Assistant Examiner*—James H. Reamer

[57] ABSTRACT

A process is provided for preparing quaternary ammonium compounds which contain both cationic and nonionic hydrophilic groups in the molecule. Alkylene oxide is reacted with aliphatic alcohol in the presence of an alkali catalyst at an elevated temperature; the resulting alkoxyglycol alcohol or ether is reacted with epichlorohydrin, producing the corresponding chloroglyceryl or chlorohydroxypropylene ether; and this is then reacted with a secondary amine to produce the quaternary ammonium compound.

10 Claims, No Drawings

PROCESS FOR PREPARING QUATERNARY AMMONIUM COMPOUNDS

This application is a continuation-in-part of Ser. No. 306,251, now abandoned filed Nov. 10, 1972, and Ser. No. 423,592, filed Dec. 10, 1973.

U.S. Pat. Nos. 3,395,708 and Re. No. 26,939, to Hervey and George, dated Aug. 6, 1968 and Aug. 18, 1970, and French Pat. No. 1,265,818, disclose that treatment of unfiberized wet cellulose pulp with a surfactant before or during the formation of the cellulose pulp on a drying machine or on a paper machine reduces the interfiber bonds of the cellulose. The improvement is accomplished by impregnating a wet slurry of wood pulp with a cationic debonding agent, forming the wet slurry into a wet pressed wood pulp sheet, and mechanically fiberizing the dried sheet to form a substantially completely fiberized fluffed fibrous wood pulp batt. The result of this treatment is a cellulose batt, sheet or paper having improved softness and a low degree of mechanical strength. Among the surfactants said to be useful in this way are long chain cationic surfactants, preferably with at least twelve carbon atoms in at least one alkyl chain, and illustrative, but non-limiting, specific examples of same are fatty dialkyl amine quaternary salts, mono fatty alkyl tertiary amine salts, primary amine salts, and unsaturated fatty alkyl amine salts.

The hydrophilic cationic portion of the surfactant is considered to be attracted to the negatively-charged cellulose fibers, while the hydrophobic portions of the molecule are exposed on the surface, thus rendering the surface of the fibers hydrophobic. The interbonds between the cellulose fibers are reduced, and the defibration into cellulose fluff is thereby facilitated. However, a highly hydrophilic cellulose pulp when treated with such cationic surfactants will exhibit more hydrophobic properties than the corresponding untreated cellulose pulp. If the cellulose pulp or paper is intended to be used in the production of highly absorbent products, such as sanitary products, hydrophobicity is not desirable, since it reduces absorptivity. Consequently, in the treatment of such cellulose derivatives, it has been necessary in order to improve the wettability of the cellulose fibers after the treatment to add a wetting agent, which is preferably added to the cellulose pulp sheet in a separate operation, owing to the low degree of affinity to cellulose of these wetting agents.

In accordance with the invention of Ser. No. 306,251, filed Nov. 10, 1972, it has been determined that bis(alkoxy (2-hydroxy)propylene) quaternary ammonium compounds which contain both cationic and nonionic hydrophilic groups when used to treat textile materials impart improved softness and excellent antistatic properties while at the same time preserving good hydrophilic properties. The quaternary ammonium compounds in accordance with the invention have the general formula:

Cation Anion

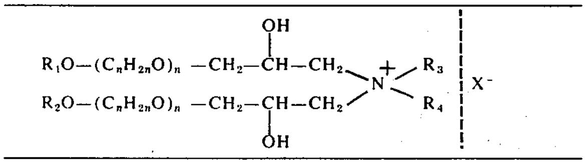

In this formula:

$R_1$ and $R_2$ are aliphatic hydrocarbon groups, which can be either saturated or unsaturated, having from about eight to about twenty-two carbon atoms.

$R_3$ and $R_3$ are methyl, ethyl or hydroxyethyl.

n is a number from 2 to 4, representing the number of carbon atoms in the oxyalkylene substituent, which can thus be oxyethylene, oxypropylene-1,2or -1,3 or oxybutylene-1,2 -1,3, -1,4 or -2,3.

$n_1$ And $n_2$ are numbers within the range from 0 to about 10, representing the number of oxyalkylene groups present in each substituent, $n_1$ and $n_2$ usually represent average values, and therefore need not be integers.

X is a salt-forming anion, and can be organic or inorganic.

The quaternary ammonium compounds in accordance with the invention of Ser. No. 306,251 impart superior antistatic properties to substrates than the alkyl quaternary ammonium compounds heretofore used, such as those of U.S. Pat. No. 3,395,708. The improvement in antistatic properties is believed due to the presence of the 2-hydroxy-oxypropylene group. The addition of the oxyalkylene units also improves antistatic properties as well as softening properties. Compounds having no or from one to two oxyalkylene groups and one 2-hydroxy-oxypropylene group attached to the aliphatic hydrocarbon group impart the best antistatic and softening properties, and are therefore preferred. In these compounds, $n_1$ and $n_2$ are numbers within the range from 0 to 2.

The quaternary compounds in accordance with the invention of Ser. No. 306,251 can be applied to the substrate in the form of solutions, in water or in an organic solvent. In such solutions, the concentration of quaternary ammonium compound can range from about 0.01 to about 25%, preferably from 0.1 to about 10%.

In accordance with the instant invention, a process is provided for preparing alkoxy 2-hydroxypropylene quaternary ammonium compounds by reaction of alkylene oxide with aliphatic alcohol to form the corresponding alkoxy glycol alcohol or ether, followed by reaction of this product with epichlorhydrin producing the corresponding chloroglyceryl or chlorohydroxypropylene ether, which is then reacted with a secondary amine.

The synthesis of the alkoxy-2-hydroxy-propylene quaternary ammonium compounds in accordance with the invention includes the following reaction steps:

1)

2)

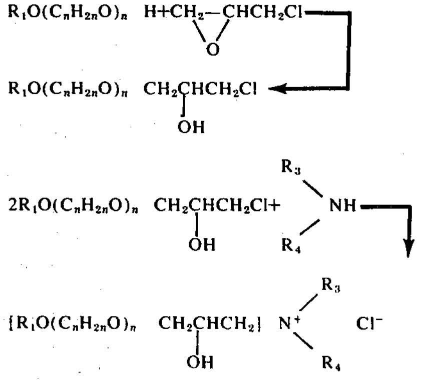

In the above reaction formulae, $R_1$, $R_3$, $R_4$, $n$ and $n_1$ have the meaning earlier mentioned.

The alkoxyalkylene oxy-(2-hydroxy)propylene quaternary ammonium compounds in accordance with the invention can be prepared by reaction of from one to about ten mols of ethylene oxide with one mol of an aliphatic alcohol having from about eight to about twenty-two carbon atoms. The reaction of alkylene oxide with the alcohol is carried out in the presence of an alkali catalyst, preferably sodium hydroxide, at an elevated temperature. If no oxyalkylene unit is present, of course this reaction step is omitted.

The resulting alkoxy glycol ether (or the alcohol, if no oxyalkylene group is present) is reacted with epichlorhydrin, producing the corresponding chloroglyceryl or chlorohydroxypropylene ether, which is then reacted with a secondary amine having the formula $R_3R_4NH$, where $R_3$ and $R_4$ are methyl, ethyl, or hydroxyethyl.

The product is a quaternary ammonium compound of the invention, in the form of its chloride salt. The chloride ion can then be exchanged by another anion, using known techniques, for example, by addition of a sodium salt with a higher solubility constant than sodium chloride, or by ion exchange in an anion exchanger. Among anions other than chloride ion which can serve as X in the quaternary ammonium compounds of the invention are nitrate, carbonate, hydroxyl, phosphate, iodide, bromide, methyl, sulfate, acetate, carbonate, formate, citrate, propionate, and tartrate. The monovalent anions are preferred.

The reaction between the alkylene oxide adduct and the epichlorhydrin proceeds at an elevated temperature within the range from about 25° to about 150°C in the presence of a catalyst, such as stannic chloride, boron trifluoride, and perchloric acid, $HClO_4$. These give a rapid easily controllable reaction, but other acid catalysts such as toluene sulfonic acid and sulfuric acid can also be used.

In order to ensure complete reaction of the alkylene oxide adduct, an excess of epichlorhydrin is generally added.

The quaternization of the secondary amine with the chloroglyceryl ether is carried out in the presence of alkali, generally sodium hydroxide, at an elevated temperature within the range from about 25° to about 150°C, in the presence of water or a water miscible organic solvent.

It is not necessary that the organic solvent be miscible with water in all proportions, but it should be miscible with water in the proportions used so as to form a homogeneous solvent mixture, if water is also present.

Any water-miscible organic solvent which is inert under reaction conditions can be used. The organic solvent accordingly can be selected from the classes consisting of lower aliphatic alcohols having from one to about six carbon atoms, lower aliphatic polyhydric alcohols having from two to about six carbon atoms and from two to six hydroxyl groups, and monoalkyl ethers of such lower aliphatic polyhydric alcohols having from two to about six carbon atoms in the alkyl group; polyoxyalkylene glycols and polyoxyalkylene glycol monoethers having at least one oxyether linkage and two alkylene groups, the alkylene groups having from two to four carbon atoms in a straight or branched chain, and having not more than one hydroxyl group etherified with a lower alkyl group having from one to about six carbon atoms; and heterocyclic ethers having up to six ring atoms of which one or two may be ether oxygen, and four or five carbon atoms.

Exemplary lower aliphatic alcohols include methanol, ethanol, propanol, isopropanol, butanol, isobutanol, tertiarybutanol, secondary butanol, pentanol, isopentanol, hexanol, isohexanol, and tertiaryhexanol.

Exemplary polyoxyalkylene glycols and glycol ethers include the monoethyl ethers of diethylene glycol, diethylene glycol, triethylene glycol, tetraethylene glycol, the monomethyl ether of triethylene glycol, dipropylene glycol, dibutylene glycol, tributylene glycol, tetrabutylene glycol, tetrapropylene glycol, the monomethyl ether of dipropylene glycol, and the monomethyl ether of dibutylene glycol.

Examplary polyhydric alcohols include ethylene glycol, propylene glycol, butylene glycol, the monomethyl ethers of ethylene glycol, propylene glycol and butylene glycol, and the monoethyl ethers of ethylene glycol, propylene glycol and butylene glycol, glycerol, sorbitol, pentaerythritol, and neopentyl glycol.

It is also possible to react the chloroglyceryl ether with ammonia or with a primary amine having a methyl, ethyl, or hydroxyethyl group, and the resulting product may then be quaternized with methyl or ethyl chloride or dimethyl or diethyl sulfate. However, this procedure is more complicated than the previously described procedure, and it involves more reaction steps, and results in larger amounts of byproducts and lower total yields of the desired quaternary ammonium compounds.

Alkylene oxides which can be used include ethylene oxide; propylene oxide-1,2; propylene oxide-1,3; butylene oxide-1,2; butylene oxide-1,3; butylene oxide-2,3; butylene oxide-1,4.

The aliphatic alcohols having from about eight to about twenty-two carbon atoms which can be used in the reaction products of the invention include both saturated and unsaturated alcohols, such as octyl alcohol, decyl alcohol, lauryl alcohol, myristyl alcohol, cetyl alcohol, stearyl alcohol, eicosyl alcohol, oleyl alcohol, ricinoleyl alcohol, linoleyl alcohol, and eicosenyl alcohol. The alcohol can also be a mixture of such alcohols, such as are obtained from natural fats and oils by reduction of the fatty acid or fatty acid ester mixtures obtained from such oils, such as coconut oil fatty alcohols, palm oil fatty alcohols, soya oil fatty alcohols, linseed oil fatty alcohols, corn oil fatty alcohols, castor oil fatty alcohols, fish oil fatty alcohols, whale oil fatty alcohols, tallow fatty alcohols, and lard fatty alcohols. Mixtures of synthetic alcohols prepared by the Ziegler procedure or the Oxo process can also be used. Most alcohols manufactured by the Oxo process have a branched chain, which makes possible a large number of isomers. The physical properties of these alcohol mixtures are very similar to those of the straight-chain primary alcohols.

Secondary amines which can be used in accordance with the invention include dimethyl amine, diethyl amine, diethanol amine, methyl amine, and methyl hydroxyethyl amine. Primary amines which can be used include methyl amine, ethyl amine, and hydroxy-ethyl amine.

The quaternary compounds in accordance with the invention can be applied to the substrate in the form of solutions, in water or in an organic solvent. In such solutions, the concentration of quaternary ammonium compound can range from about 0.01 to about 25%, preferably from 0.1 to about 10%.

In the case of solutions for application to textile materials, the concentration of the quaternary ammonium compound can be within the range from about 0.01 to about 0.5 gram, and preferably from about 0.5 to about 0.15 gram, per liter of solution. Aqueous solutions of such concentrations are quite useful, for example, as rinsing solutions at any of the stages of textile processing during which aqueous rinsing solutions are used. Due to their good affinity for textile fibers, the quaternary ammonium compounds can be introduced into any rinsing solution in the course of the process, but the best and most lasting effect is obtained if the quaternary ammonium compound is included in the last rinsing solution.

The compounds can also be added at the prewash or in the main wash operations, but in these cases the antistatic and softening effects may be less per unit weight of compound applied to the textile material, probably because of losses of the compound during later processing.

The usual solvent used is water. However, if rapid volatilization of the solvent is desired, the quaternary ammonium compounds of the invention can be applied from a solution in a rapidly volatilizable organic solvent, such as acetone, methanol, ethanol, isopropanol, or mixtures thereof. In this case, the concentrations are the same as aqueous solutions within the range from about 0.005% to about 10% by weight of the quaternary ammonium compound.

The solutions of the quaternary ammonium compounds of the invention can also be applied by dipping, spraying or coating, using conventional techniques. This sort of application is useful on textile materials which normally are very seldom washed, or are not washed at all, or on leather or plastic sheet material, or on plastic films coated on other base such as wood. When applied in this way, the composition usually contains the quaternary ammonium compound in a concentration within the range from about 0.005% to about 10%.

The application solution can also include nonionic surfactants, such as adducts of ethylene oxide or propylene oxide and aliphatic alcohols or alkyl phenols, to improve the rewettability of the treated material. Solubility-enhancing additives, such as monoethyl ether of diethylene glycol, can also be added.

The quaternary ammonium compounds of the invention are applied to the substrate in an amount within the range from about 0.001% to about 2% by weight of the substrate.

The compounds of the invention will improve softness and impart antistatic properties to textile materials of all kinds including both woven and nonwoven materials made of natural or synthetic fibers or mixtures thereof, such as, for example, rayon, acetate rayon, cellulose acetate-propionate, cellulose acetate-butyrate, polyvinyl chloride, polyamide, polypropylene, polyethylene, polyacrylonitrile, polyesters such as ethylene glycol-terephthalic acid polymers, cotton, linen, jute, ramie, sisal, wool, mohair, alginate fibers, zein fibers, glass, potassium titanate, bast, bagasse, polyvinylidene chloride, and fur fibers of various kinds such as beaver, rabbit, seal, muskrat, otter, mink, caracul, lamb and squirrel.

The textile materials can take any form, including nonwoven materials such as felts, bats and mats; woven materials such as fabrics, cloth, carpets, rugs and upholstery; synthetic fur materials; curtains, and covering materials of all kinds.

The compounds of the invention are applicable to improve softness and impart antistatic properties to leather materials, such as leather furniture and leather clothing.

They are also applicable to plastic surfaces, many of which have a pronounced tendency to develop a static charge, such as synthetic phonograph records which are usually made of polyvinyl chloride; to painted, varnished and lacquered surfaces which bear a synthetic resinous coating film; to metal foils, and chassis for electric and electronic devices, such as radios, hi-fis, phonograph systems, sound amplification systems, amplifiers, television, and sound-recording equipment.

The following Examples in the opinion of the inventors represent preferred embodiments of their invention.

PREPARATION OF ADDITIVES

Additive A

In a reaction vessel provided with a heating coil, a stirrer, and a reflux condenser for cooling, was placed 300 grams (1 mol) of a melt of tallow fatty alcohol (a mixture of cetyl, stearyl and eicosyl alcohols), which has previously been reacted with 0.5 mol of ethylene oxide per mol of alcohol. The melt was brought to 75°C with stirring, whereupon 3 grams of stannic chloride was introduced, and 101 grams (1.1 mol) epichlorhydrin was then added over one hour. After all of the epichlorhydrin had been added, the temperature was increased to 125°C, and held there for a further reaction time of 2 hours. The remaining epichlorhydrin was then removed under vacuum, and the reaction product obtained was 390 grams of a pale yellow viscous liquid.

In an autoclave fitted with a heater and a stirrer was placed 350 grams (0.9 mol) of this reaction product, 125 grams of ethanol, in which 20 grams (0.45 mol) of dimethyl amine had been dissolved, and 23 grams (0.56 mol) of sodium hydroxide dissolved in 15 grams of water. The mixture was held at 125°C in the autoclave for 3 hours. At the conclusion of this time, the unreacted dimethyl amine was removed by bubbling nitrogen gas through the mixture. The reaction product was a pale beige substance, having a melting point of 37° to 40°C. Analysis showed that it contained 57% quaternary amine, 10% tertiary amine, 23 grams ethanol, 6% sodium chloride and 4% water, and had the formula:

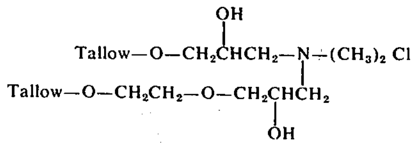

Additive B

Using the above procedure, 2 mols of alcohol, 2 mols epichlorhydrin and 1 mol dimethyl amine were reacted, to form the product:

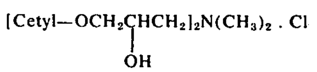

Additive C

Using the above procedure, 2 mols of tallow fatty alcohol, 2 mols of epichlorhydrin and 1 mol dimethyl amine were reacted to form the product:

$$[\text{Tallow}-O-CH_2\underset{\displaystyle OH}{\underset{|}{C}}HCH_2]_2N(CH_3)_2\cdot Cl$$

Additive D

Using the above procedure, 2 mols tallow fatty alcohol, 1 mol butylene oxide, 2 mols epichlorhydrin and 1 mol dimethyl amine were reacted to form the product:

$$[\text{Tallow}-[O-CH_2CH_2CH_2CH]_{0.5}O-CH_2\underset{\displaystyle OH}{\underset{|}{C}}HCH_2]_2N(CH_3)_2\cdot Cl$$

Additive E

Using the above procedure, 2 mols tallow fatty alcohol, 4 mols ethylene oxide, 2 mols epichlorhydrin and 1 mol dimethyl amine were reacted to form the product:

$$[\text{Tallow}-[O-CH_2CH_2]_2\ O-CH_2\underset{\displaystyle OH}{\underset{|}{C}}HCH_2]_2\ N(CH_3)_2\cdot Cl$$

Additive F

Using the above procedure, 2 mols tallow fatty alcohol, 8 mols ethylene oxide, 2 mols epichlorhydrin and 1 mol dimethyl amine were reacted to form the product:

$$[\text{Tallow}-[O-CH_2CH_2]_4\ O-CH_2\underset{\displaystyle OH}{\underset{|}{C}}HCH_2]_2\ N(CH_3)_2\cdot Cl$$

Additive G

Using the above procedure, 2 mols of a mixture of $C_{20}$ and $C_{22}$ fatty alcohols, 8 mols ethylene oxide, 2 mols epichlorhydrin and 1 mol dimethyl amine were reacted to form the product:

$$[C_{20-22}\ H_{41-43}[O-CH_2CH_2]_4O-CH_2\underset{\displaystyle OH}{\underset{|}{C}}HCH_2]\ N(CH_3)_2\cdot Cl$$

Additive H

Using the same procedure as in Additive A above, a fatty alcohol mixture (1 mol, 15% decyl alcohol, 47% dodecyl alcohol and 38% tetradecyl alcohol), was reacted with epichlorhydrin (1.1 mols) and dimethyl amine (0.5 mol), using monoethyl ether of dialkylene glycol as the solvent. The product by analysis contained 57% quaternary ammonium compound in accordance with the invention, having the formula:

$$[C_{10-12-14}\ H_{23-25-27}-O-CH_2\underset{\displaystyle OH}{\underset{|}{C}}HCH_2]_2\ N(CH_3)_2\cdot Cl$$

In addition, the reaction mixture contained 2.8% of a tertiary amine containing an alkyl ether group and two methyl groups and 25% monoethyl ether of diethylene glycol. The remainder was water, sodium chloride, and unreacted starting material. The product mixture had a softening point of 12°C, became clear at 33°C, and when allowed to cool had a hardening point of 10°C.

Twelve parts by weight of this reaction product was dissolved in 88 parts by weight of water. The resulting solution was liquid at room temperature; it became solid at 0°C. When cooled further, so that the water solution was frozen, and then thawed, no tendency towards gelation was noted.

EXAMPLES 1 TO 5

A sequence of washing tests was carried out, using cotton terry cloth as a sample textile material, and comparing Additives A to E, inclusive, with a commercial additive Arquad 2 HT 75, distearyl dimethyl ammonium chloride, a compound described in U.S. Pat. No. 3,395,708. A drum washing machine was used. The test swatches of cotton terry cloth were washed with a commercial detergent at 90°C, the same detergent solution being used in all tests. In the last rinsing water, one of the Additives A to E or the commercial product, distearyl dimethyl ammonium chloride, was introduced in an amount corresponding to 0.5 gram per kilogram of cloth samples. The washing and the after treatment were repeated five times. After each washing, the softness of the terry cloth was subjectively judged by a panel of six persons. The following results were obtained:

TABLE I

| | | | Number of persons considering: | | |
|---|---|---|---|---|---|
| Ex. No. | Additive | Washing Set | Commercial best additive | Additives Equivalent | Additives according to invention best |
| 1 | A | 1 | 0 | 1 | 5 |
| | | 2 | 0 | 1 | 5 |
| | | 3 | 1 | 0 | 5 |
| | | 4 | 0 | 0 | 6 |
| | | 5 | 0 | 0 | 6 |
| 2 | B | 1 | 2 | 2 | 2 |
| | | 2 | 1 | 3 | 2 |
| | | 3 | 2 | 1 | 3 |
| | | 4 | 1 | 2 | 3 |
| | | 5 | 0 | 3 | 3 |
| 3 | C | 1 | 1 | 1 | 4 |
| | | 2 | 1 | 1 | 4 |
| | | 3 | 0 | 2 | 4 |
| | | 4 | 0 | 1 | 5 |
| | | 5 | 0 | 1 | 5 |
| 4 | D | 1 | 0 | 0 | 6 |
| | | 2 | 0 | 0 | 6 |
| | | 3 | 0 | 0 | 6 |
| | | 4 | 0 | 0 | 6 |
| | | 5 | 0 | 0 | 6 |
| 5 | E | 1 | 2 | 3 | 1 |
| | | 2 | 2 | 3 | 1 |
| | | 3 | 2 | 2 | 2 |
| | | 4 | 2 | 2 | 2 |
| | | 5 | 1 | 3 | 2 |

From the above results, it is evident that the Additives A and D were regarded as having the best softening properties, and were clearly better than the commercial additive. The Additives B and C, without ethylene glycol units, also showed good softening properties, and were clearly better than the commercial additive. the data for Additive E show that if the number of ethylene glycol units is increased over about one unit per chain, the softening effect decreases, since at two units per chain, a softening effect comparable to the commercial additive is obtained.

EXAMPLES 6 TO 12

The antistatic properties of Additives A to G above were evaluated in comparison with Arquad 2 HT 75, distearyl dimethyl ammonium chloride, using a sequence of washing tests in a drum washing machine and test swatches of nylon cloth as the textile material. The test swatches were washed with the same commercial nonsoap detergent in each test, at 22°C. In the last rinsing water, a solution of one fo the additives was used in an amount corresponding to 0.5 gram per kilogram of nylon. After treatment, the time required for discharge of half the electric charge applied to the nylon in a Rothschild Static Voltmeter R-1020 was determined. The following results were obtained:

TABLE II

| Example No. | Additive | Half-life (seconds) |
|---|---|---|
| Control | Commercial product | 12 |
| 6 | A | 6 |
| 7 | B | 10 |
| 8 | C | 10 |
| 9 | D | 6 |
| 10 | E | 5 |
| 11 | F | 6 |
| 12 | G | 6 |

It is apparent from the above results that Additives B and C, which do not contain oxyethylene units, have better antistatic properties than the commercial additive. The addition of oxyethylene units improved (Additives A, D, E, F and G) the antistatic effect so that the half-line for the nylon swatches treated with these additives is half or less that for the commercial additive.

It is apparent from these data that the quaternary ammonium compounds in accordance with the invention have a better antistatic effect than the closely-related quaternary ammonium compounds of the prior art. It is further evident that the compounds wherein $n_1$ and $n_2$ are within the range from 0 to 2 have superior properties, both in antistatic effect and in softening effect.

EXAMPLE 13

The softening and antistatic properties of Additive H were evaluated against distearyl dimethyl ammonium chloride, Arquad 2 HT 75, for comparison. Test swatches of cotton terry cloth were washed with commercial nonsoap detergent at 90°C in a drum washing machine. The last rinsing water contained either the Additive H or the distearyl dimethyl ammonium chloride, applying 1.2 grams of dry additive per kilogram of cotton terry cloth swatches. This washing cycle was repeated five times. After each washing cycle, the softness of the pieces of terry cloth was judged subjectively by six persons. Three of them found the pieces of terry cloth which had been treated with the quaternary ammonium compound of the invention to be the softest, while three of them did not notice any difference.

The water absorpitivity of the treated terry cloth swatches was determined by pressing a circular testing piece against the upper surface of a glass fiber while the entire under surface was in contact with water. By measuring the decrease in the amount of water as a function of time, the water absorption was determined. The following results were obtained:

TABLE III

| | Water Absorption ml of water/g cloth absorbed after 50 secs. |
|---|---|
| Untreated terry cloth | 3.1 |
| Terry cloth treated with 1.2 g/kg of distearyl dimethyl ammonium chloride | 1.1 |
| Terry cloth treated with 1.2 g/kg of the cation surfactant according to the invention | 2.3 |

Antistatic properties were evaluated on nylon cloth swatches which had been washed at 20°C, using a nonsoap synthetic detergent with the additive in accordance with the invention added to the last rinse in the same manner as in Examples 6 to 12. After conditioning the nylon swatches for 24 hours at a relative humidity of 65% and 20°C, the time required for discharge of half the electric charge applied to the nylon in a Rothschild Static Voltmeter R-1020 was determined. A strip of the cloth was stretched between two metal clips, to which a potential of 100 volts was applied. The following results were obtained.

TABLE IV

| Product | Half-life (seconds)[1] |
|---|---|
| Untreated nylon cloth | 74 |
| Nylon cloth treated with 1.2 g/kg of distearyl dimethyl ammonium chloride | 34 |
| Nylon cloth treated with 1.2 g/kg of the cation surfactant according to the invention | 10 |

[1]Due to different testing conditions, no direct comparison with the results from Examples 6 to 12 can be made.

The above data show that this compound is a liquid at room temperature, and forms a freeze-thaw-stable aqueous solution at a concentration of 12%. Compared to distearyl dimethyl ammonium chloride, the quaternary ammonium compound according to the invention imparts improved softening, antistatic and water-absorption effects to the textile material treated.

Having regard to the foregoing disclosure, the following is claimed as the inventive and patentable embodiments thereof:

1. A process for the preparation of alkoxyalkylene oxy(2-hydroxy)propylene quaternary ammonium compounds having the formula:

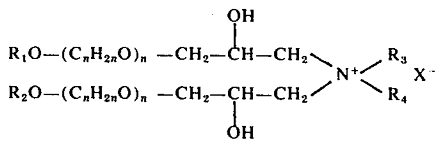

in which $R_1$ and $R_2$ are aliphatic hydrocarbon groups having from about eight to about twenty-two carbon atoms.

$R_3$ and $R_4$ are selected from the group consisting of methyl, ethyl and hydroxyethyl.

*n* is a number from 2 to 4, representing the number of carbon atoms in the oxyalkylene substituent, $n_1$ and $n_2$ are numbers within the range from 0 to about 10, representing the number of oxyalkylene groups present in each substituent; and X is a salt-forming anion; which comprises reacting from zero to about ten mols of alkylene oxide with one mol of an aliphatic alcohol having from about eight to about 22 carbon atoms, in the presence of an alkaline catalyst at an elevated temperature within the range from about 25° to 150°C, reacting the resulting alkoxy glycol ether or aliphatic alcohol, if no oxyalkylene group is present, with epichlorohydrin, producing the corresponding chloroglyceryl or chlorohydroxypropylene ether, and then reacting this ether with a secondary amine having the formula $R_3R_4NH$, where $R_3$ and $R_4$ are selected from the group consisting of methyl, ethyl and hydroxyethyl in the presence of alkali and in the presence of a solvent selected from the group consisting of water and inert water-miscible organic solvents at an elevated temperature within the range from about 25° to 150°C, until there is obtained the quaternary ammonium compound of the above formula in the form of its chloride salt.

2. A process according to claim 1, which comprises exchanging the chloride anion by another anion.

3. A process according to claim 1, in which the reaction between the alkylene oxide adduct and the epichlorohydrin is carried out in the presence of a catalyst selected from the group consisting of stannic chloride, boron trifluoride, perchloric acid $HClO_4$, toluene sulfonic acid and sulfuric acid.

4. A process according to claim 1, in which the solvent during quaternization is selected from the group consisting of methanol, ethanol, and the monoethylether of diethylene glycol.

5. A process according to claim 1, in which $n_1$ and $n_2$ are each zero.

6. A process according to claim 1 in which $n_1$ and $n_2$ are each numbers from 2 to 10.

7. A process according to claim 1 in which $n$ is 2.

8. A process according to claim 1 in which $n$ is 3.

9. A process according to claim 1 in which the alkali is sodium hydroxide.

10. A process according to claim 1 in which the solvent is water.

* * * * *

PO-1050
(5/69)

UNITED STATES PATENT OFFICE

CERTIFICATE OF CORRECTION

Patent No. 3,932,495 Dated January 13, 1976

Inventor(s) Eva Margareta Martinsson

It is certified that error appears in the above-identified patent and that said Letters Patent are hereby corrected as shown below:

Column 1, line 65 :

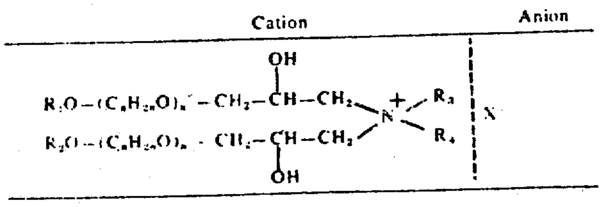

should be

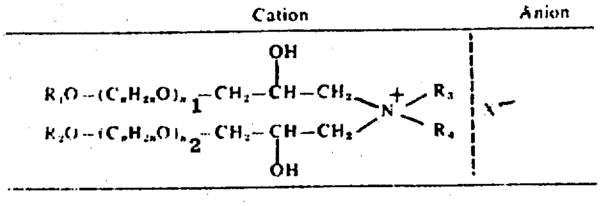

Column 2, line 9 : "1,2or" should be --1,2 or--

Column 2, line 11 : "And" should be --and--

UNITED STATES PATENT OFFICE

CERTIFICATE OF CORRECTION

Patent No. 3,932,495 Dated January 13, 1976

Inventor(s) Eva Margareta Martinsson

It is certified that error appears in the above-identified patent and that said Letters Patent are hereby corrected as shown below:

Column 2, line 62 :

1) 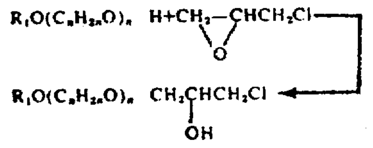

2) 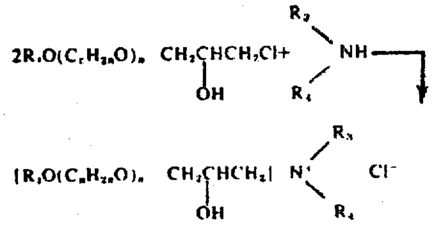

should be

1) 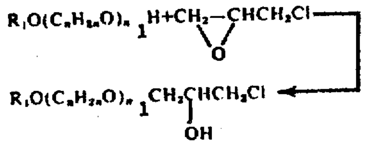

2) 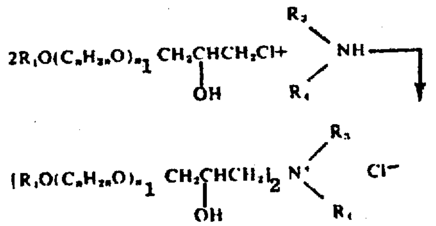

Column 8, line 66 : "the" should be --The--

UNITED STATES PATENT OFFICE

CERTIFICATE OF CORRECTION

Patent No. 3,932,495 Dated January 13, 1976

Inventor(s) Eva Margareta Martinsson

It is certified that error appears in the above-identified patent and that said Letters Patent are hereby corrected as shown below:

Column 10, line 56 :

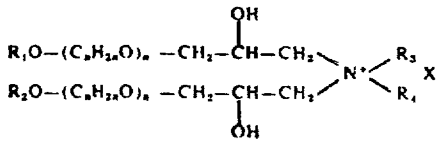

should be

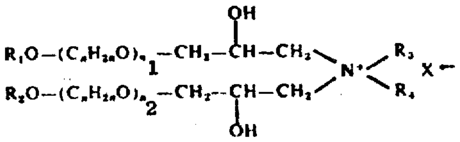

Signed and Sealed this

*twenty-ninth* Day of *June 1976*

[SEAL]

*Attest:*

RUTH C. MASON
*Attesting Officer*

C. MARSHALL DANN
*Commissioner of Patents and Trademarks*